(12) United States Patent
Vonk

(10) Patent No.: US 6,567,701 B2
(45) Date of Patent: May 20, 2003

(54) METHOD AND SYSTEM FOR DISCRIMINATING CAPTURED BEATS FROM NON-CAPTURED BEATS IN A CARDIAC PACING SYSTEM

(75) Inventor: Bernardus F. M. Vonk, Wehl (NL)

(73) Assignee: Medtronic, Inc., Minneapolis, MN (US)

( * ) Notice: Subject to any disclaimer, the term of this patent is extended or adjusted under 35 U.S.C. 154(b) by 298 days.

(21) Appl. No.: 09/741,351

(22) Filed: Dec. 21, 2000

(65) Prior Publication Data

US 2002/0116031 A1 Aug. 22, 2002

(51) Int. Cl.⁷ .............................................. A61N 1/365
(52) U.S. Cl. ........................................................ 607/28
(58) Field of Search .............................. 607/4, 5, 9, 11, 607/27, 28

(56) References Cited

U.S. PATENT DOCUMENTS

| | | | |
|---|---|---|---|
| 4,114,627 A | | 9/1978 | Lewyn et al. ................. 607/13 |
| 5,172,690 A | | 12/1992 | Nappholz et al. ............. 607/13 |
| 5,431,693 A | | 7/1995 | Schroeppel .................... 607/28 |
| 5,861,013 A | | 1/1999 | Peck et al. .................... 607/28 |
| 5,871,512 A | * | 2/1999 | Hemming et al. ............ 607/28 |
| 5,873,898 A | * | 2/1999 | Hemming et al. ............ 607/28 |
| 6,134,473 A | * | 10/2000 | Hemming et al. ............ 607/28 |
| 6,163,724 A | * | 12/2000 | Hemming et al. ............ 607/28 |

* cited by examiner

Primary Examiner—Willis R. Wolfe
(74) Attorney, Agent, or Firm—Thomas F. Woods; Eric R. Waldkoetter; Tom G. Berry

(57) ABSTRACT

A method of discriminating a captured beat is provided. A pulse is transmitted and an evoked response signal is received. The evoked response signal is filtered and the filtered response signal is analyzed for at least one positive signal component. Systems and devices for discriminating a captured beat are also provided.

40 Claims, 11 Drawing Sheets

METHOD AND SYSTEM FOR DISCRIMINATING CAPTURED BEATS FROM NON-CAPTURED BEATS IN A CARDIAC PACING SYSTEM

FIELD OF THE INVENTION

The present invention relates to the field of implantable medical devices. More particularly, the present invention relates to cardiac pacing systems that are capable of distinguishing captured beats from non-captured beats in a pacing system, especially a pacing system for a mammalian heart.

BACKGROUND OF THE INVENTION

Implantable pulse generators (or IPGs) are well known in the prior art. Most IPGs include sense amplifier circuitry for detecting intrinsic cardiac electrical activity so that the IPGs may be inhibited from generating unnecessary stimulating pulses when a heart is functioning properly.

Dual-chamber cardiac pacemakers typically include separate sense amplifiers for atrial and ventricular sensing. The sense amplifiers detect the presence of signals intrinsic to the heart. Two forms of these intrinsic signals occur naturally: P-waves in the atrium and R-waves in the ventricle. Upon detecting an intrinsic signal, the sense amplifier circuitry generates a digital signal to be output to other components. These components are used to inhibit the delivery of a pacing pulse to either or both chambers if P-waves and or R-waves are occurring properly in the appropriate chamber.

It is desirable to measure reliably the response of the heart evoked by an electrical stimulation pulse (e.g. a captured beat). The measurement of the evoked response permits the determination of a patient's stimulation threshold, e.g., the minimum energy a stimulating pulse must contain for a cardiac response to be evoked. Once a patient's stimulation threshold is determined, the energy content of stimulating pulses may be adjusted to avoid delivering pulses with unnecessarily high energy content. Minimizing the energy content of stimulating pulses reduces power consumption, a key concern in the context of battery-powered implantable devices. Minimizing the energy content of stimulating pulses may also reduce possible side effects such as inadvertent stimulation of the diaphragm.

Detection and measurement of the response evoked by a stimulating pulse may also be useful in controlling a pacemaker's pacing rate, in ascertaining the physiological effect of drugs or in diagnosing abnormal cardiac conditions.

There are typically two electrode-tissue interfaces in a pacing circuit: one for the tip electrode, and one for the ring (or case) electrode. Generation and delivery of an electrical heart stimulating pulse (pacing pulse) from either electrode gives rise to the storage of charge at the electrode-tissue interface. A residual post-pace polarization signal (also called stimulation polarization artifacts, "after-potentials," or polarization signals) may be generated as this stored energy dissipates after the pacing event. The tip electrode is the primary after-potential storage element in comparison to the ring electrode.

Generation and delivery of a pacing pulse may also evoke a response signal in the cardiac tissue. The evoked response signal is generally the desired result of a pacing pulse while the polarization signal is simply a residual artifact of the pacing pulse. Typically, the polarization signal may even be considered an unwanted product of the stimulus pulse. However it is difficult for conventional pacemakers to differentiate between the two. Additionally, post-pace polarization signals typically have amplitudes higher than the evoked response signal; the evoked response may thus be superimposed on the polarization signal. Consequently, it becomes difficult, if not impossible, to detect an evoked response signal using a conventional pacemaker or PCD sense amplifier employing conventional frequency filtering techniques. Polarization signals typically also have larger amplitudes than those signals intrinsic to the heart. Thus, polarization signals may also interfere with the detection and analysis of an evoked response signal in comparison to the intrinsic signals of the heart.

To overcome this difficulty, most pacemakers are set to go off-line for a certain amount of time after a stimulus has been applied. This waiting period may be termed the refractory period. The refractory period allows the polarization signal to disappear or subside to some minimal amplitude level. Unfortunately, the evoked response often also disappears or subsides during the refractory period. As a result, these pacemakers cannot detect evoked response signals with any degree of confidence. Some pacemakers are designed to come on-line after the refractory period and detect intrinsic signals (e.g., P and R waves). However, information about detected intrinsic signals does not typically provide information about the evoked response signal.

Thus, a need exists in the medical arts for determining reliably whether or not an evoked response signal has occurred in a pacing environment.

Several methods have been proposed in the prior art for improving an implantable device's ability to detect and measure evoked responses (e.g. captured beats).

For example, U.S. Pat. No. 5,861,013 to Peck et al., entitled "Peak Tracking Capture Detection Circuit and Method", hereby incorporated by reference in its entirety, discloses detecting an evoked response by noting the polarity of the positive or negative change in voltage with respect to time (or dv/dt) of a waveform incident on the lead electrodes during a period of time immediately after a pacing pulse. An evoked response may reverse the polarity of the polarization signal as detection is occurring; this reversal may be noted. If the magnitude of the polarization signal is so great that the evoked response does not reverse the polarity, an acceleration (increasing magnitude of dv/dt) in the sensed signal or waveform may be noted instead.

U.S. Pat. No. 5,172,690 to Nappholz et al., entitled "Automatic Stimulus Artifact Reduction for Accurate Analysis of the Heart's Stimulated Response," hereby incorporated by reference in its entirety, discloses a tri-phasic stimulation waveform consisting of pre-charge, stimulus, and post-charge segments. The duration of the pre-charge segment is varied until the amplitude of the stimulation artifact is small compared to the evoked response.

U.S. Pat. No. 5,431,693 to Schroeppel, entitled "Method of Verifying Capture of the Heart by a Pacemaker," hereby incorporated by reference in its entirety, discloses a pacemaker that low-pass filters a sensed signal to remove noise and pass frequencies characteristic of the evoked cardiac signal. The filtered signal is processed to render a waveform signal representing the second derivative of the filtered signal. The second derivative filtered signal is further analyzed to detect minimum and maximum amplitude excursions during selected first and second time windows. The amplitude differences measured during the two time windows are compared to one another to determine whether capture has occurred.

U.S. Pat. No. 4,114,627 to Lewyn et al., entitled "Cardiac Pacer System and Method with Capture Verification Signal," hereby incorporated by reference in its entirety, discloses a pacer that delivers output stimulating pulses through an output coupling capacitor. During delivery of a stimulating pulse, the sense amplifier is uncoupled from the cardiac electrode. When the stimulating pulse terminates, the output coupling capacitor is coupled to ground through a discharge resistor, thereby discharging electrode polarization.

As discussed above, the most pertinent prior art patents are shown in the following table:

TABLE 1

Prior Art Patents.

| Patent No. | Date | Inventor(s) |
| --- | --- | --- |
| U.S. Pat. No. 4,114,627 | 04-19-1978 | Lewyn et al. |
| U.S. Pat. No. 5,172,690 | 12-22-1992 | Nappholz et al. |
| U.S. Pat. No. 5,431,693 | 07-11-1995 | Schroeppel |
| U.S. Pat. No. 5,861,013 | 01-19-99 | Peck et al. |

All the patents listed in Table 1 are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the patents of Table 1 may be modified advantageously by using the teachings of the present invention.

SUMMARY OF THE INVENTION

The present invention is therefore directed to providing a method and system for discriminating a captured beat from a non-captured beat in cardiac tissue. Such a system of the present invention overcomes the problems, disadvantages and limitations of the prior art described above, and provides a more efficient and accurate means of distinguishing a captured beat.

The present invention has certain objects. That is, various embodiments of the present invention provide solutions to one or more problems existing in the prior art respecting the instantaneous stimulation of a mammalian heart. Those problems include, without limitation: the ability to discriminate between a captured beat and a non-captured beat.

In comparison to known techniques for determining a captured beat, various embodiments of the present invention may provide the following advantage, inter alia, i.e., the accurate distinguishing of a captured beat from a non-captured beat.

Some of the embodiments of the present invention include one or more of the following features: an implantable medical device including at least one sensing lead, at least one pacing lead, a microprocessor and an input/output circuit including a digital controller/timer circuit, an output circuit, a sense amplifier, a peak sense and threshold measurement device, a comparator and an electrogram amplifier.

Furthermore, in accordance with the present invention, an embodiment for a method and system of discriminating a captured beat from a non-captured beat in cardiac tissue is provided. A pulse is transmitted to the cardiac tissue. An evoked response signal is received. The evoked response signal is filtered and analyzed for positive signal components in a predetermined window.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

The term "captured beat" appearing herein may indicate a successfully evoked response to stimulation from a pacing pulse, particularly in cardiac tissue. Conversely, the term "non-captured beat" appearing herein may indicate an unsuccessfully evoked response to stimulation from a pacing pulse, e.g., the stimulation does not evoke any response.

Figure 1:
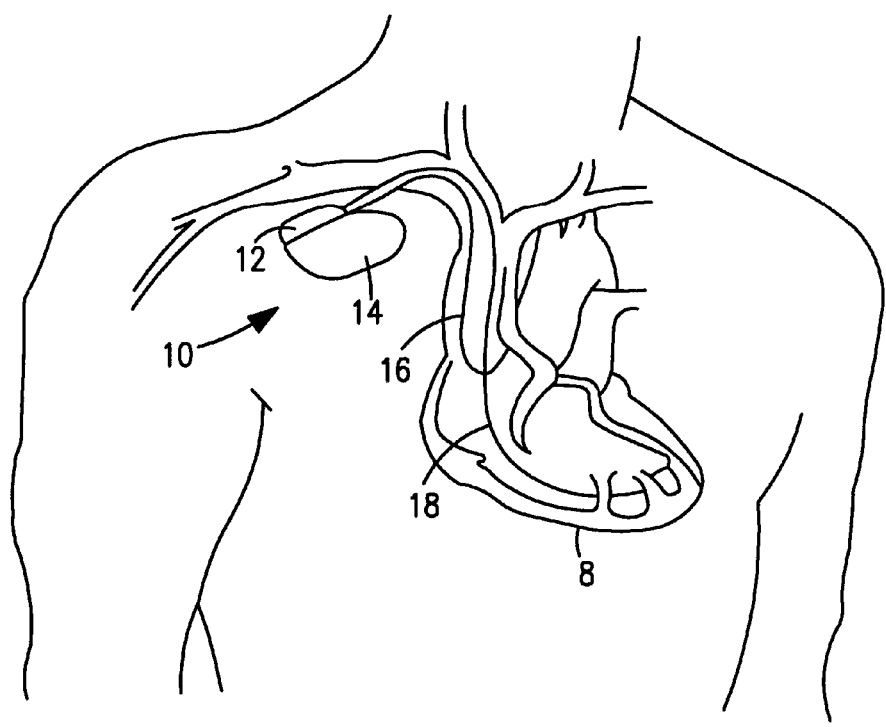
FIG. 1 is a schematic view of one embodiment of an implantable medical device in situ, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18. Leads 16, 18 may be attached to hermetically sealed enclosure 14 and may be implanted near human or mammalian heart 8. Pacing lead 16 and sensing lead 18 may sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all of which are hereby incorporated by reference, each in their respective entireties.

Figure 2:
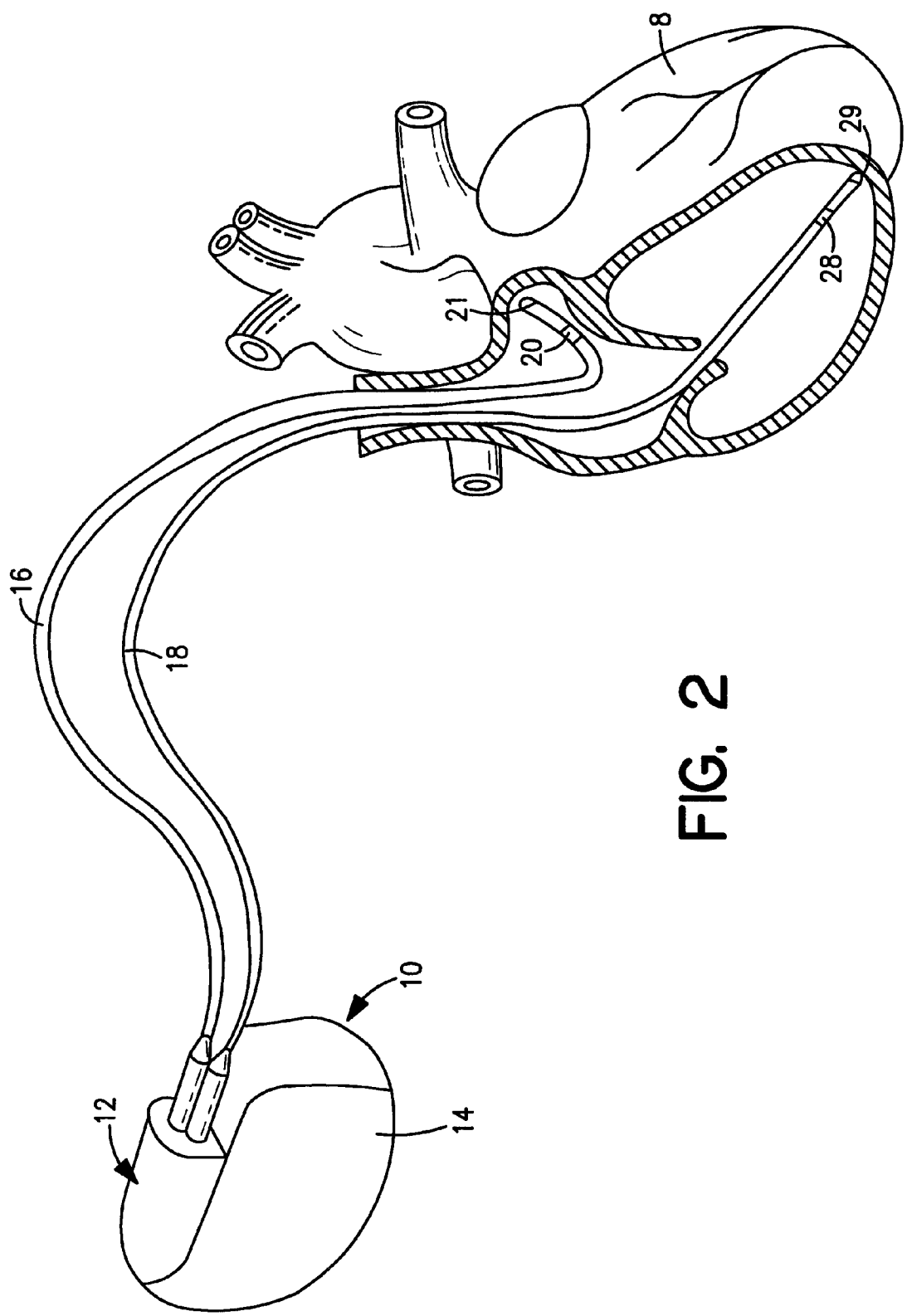
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
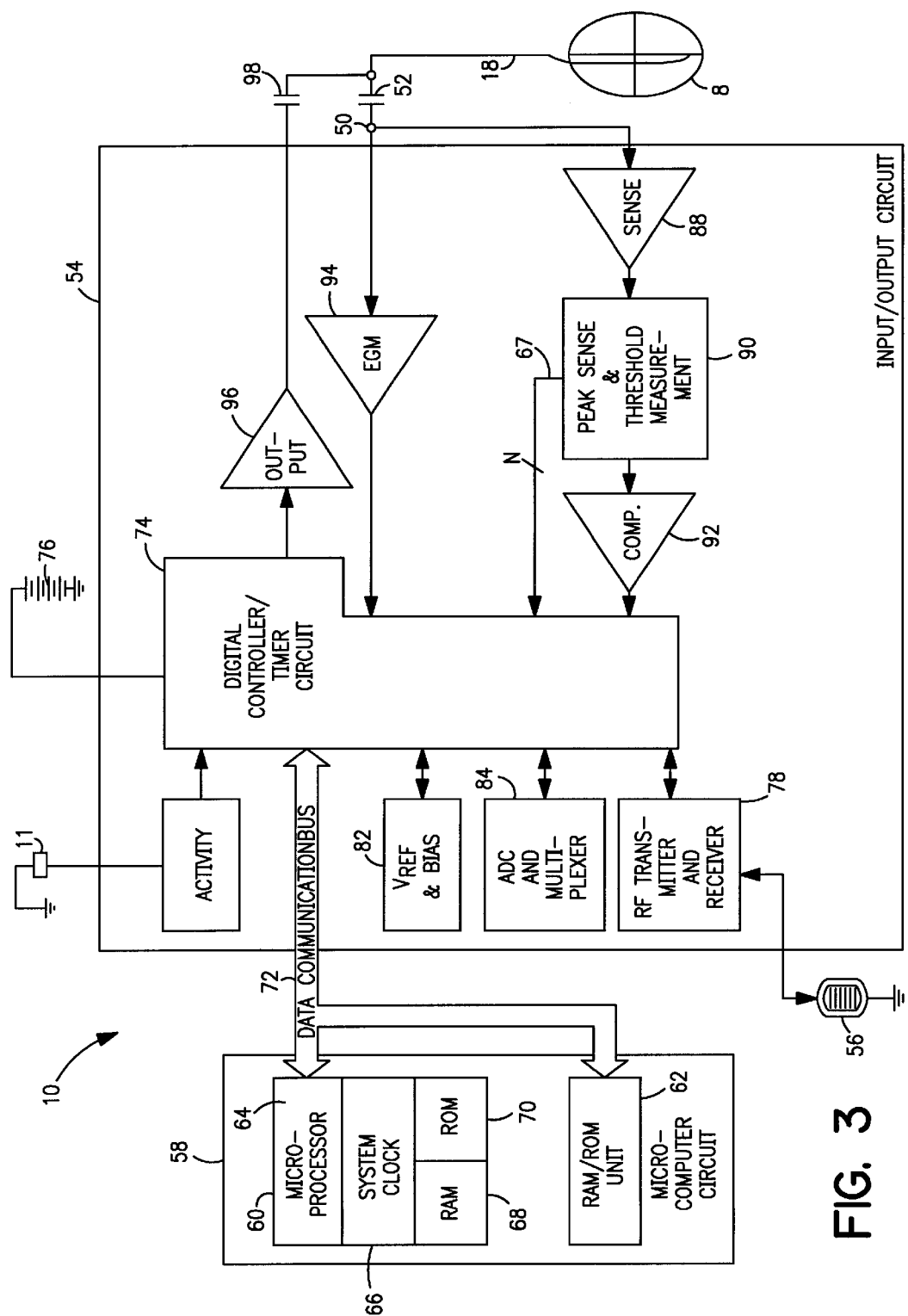
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor 11. Activity sensor 11 may be, for example, an accelerometer based on silicon technology, a piezoceramic accelerometer or an accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in the '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 may be controlled by software-implemented algorithms stored in microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 may be powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. In one embodiment of the invention, the particular programming and telemetry scheme selected permits the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD and DDI, modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
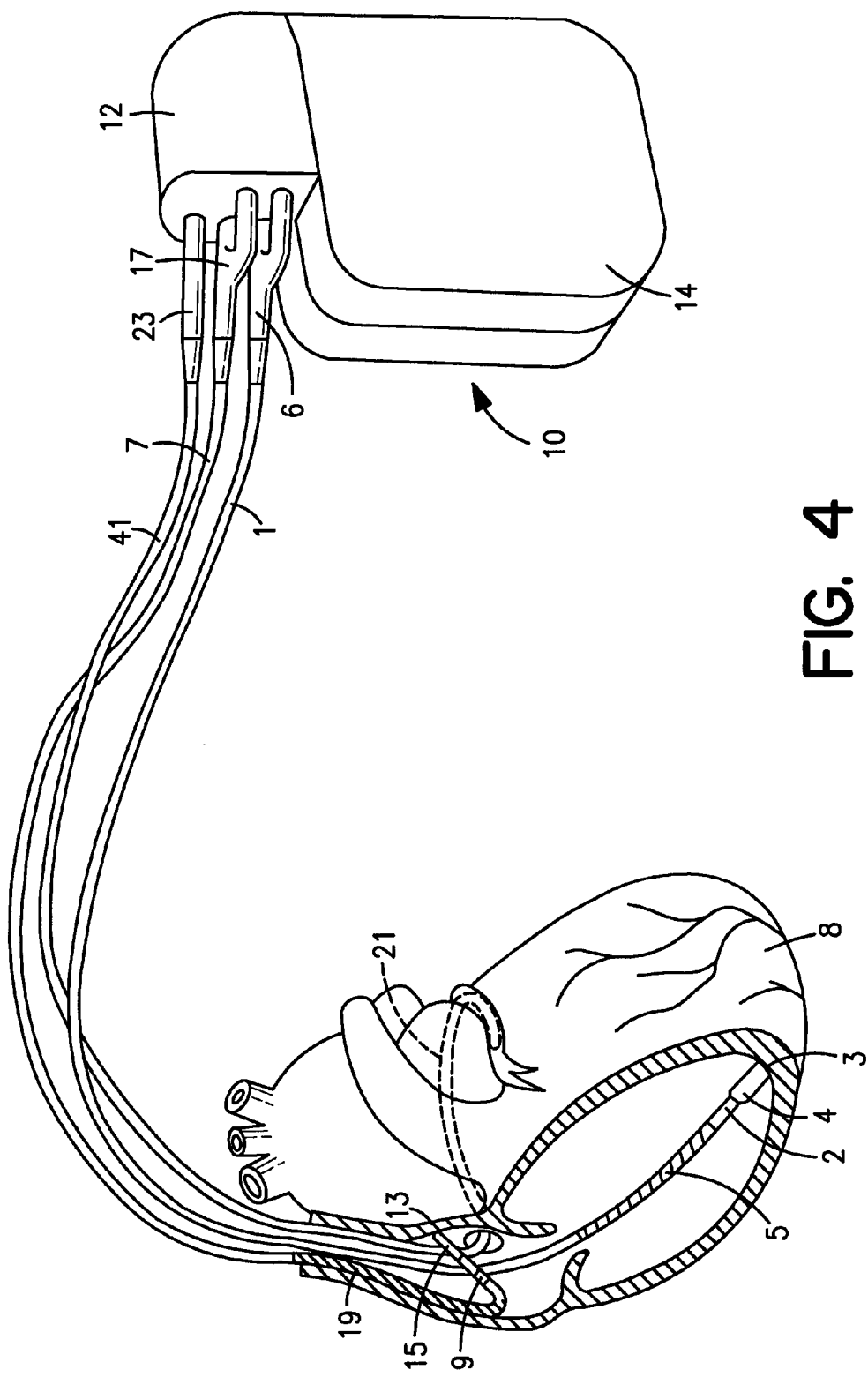
FIG. 4 is a schematic view of another embodiment of an implantable medical device, made in accordance with the present invention.
Figure 5:
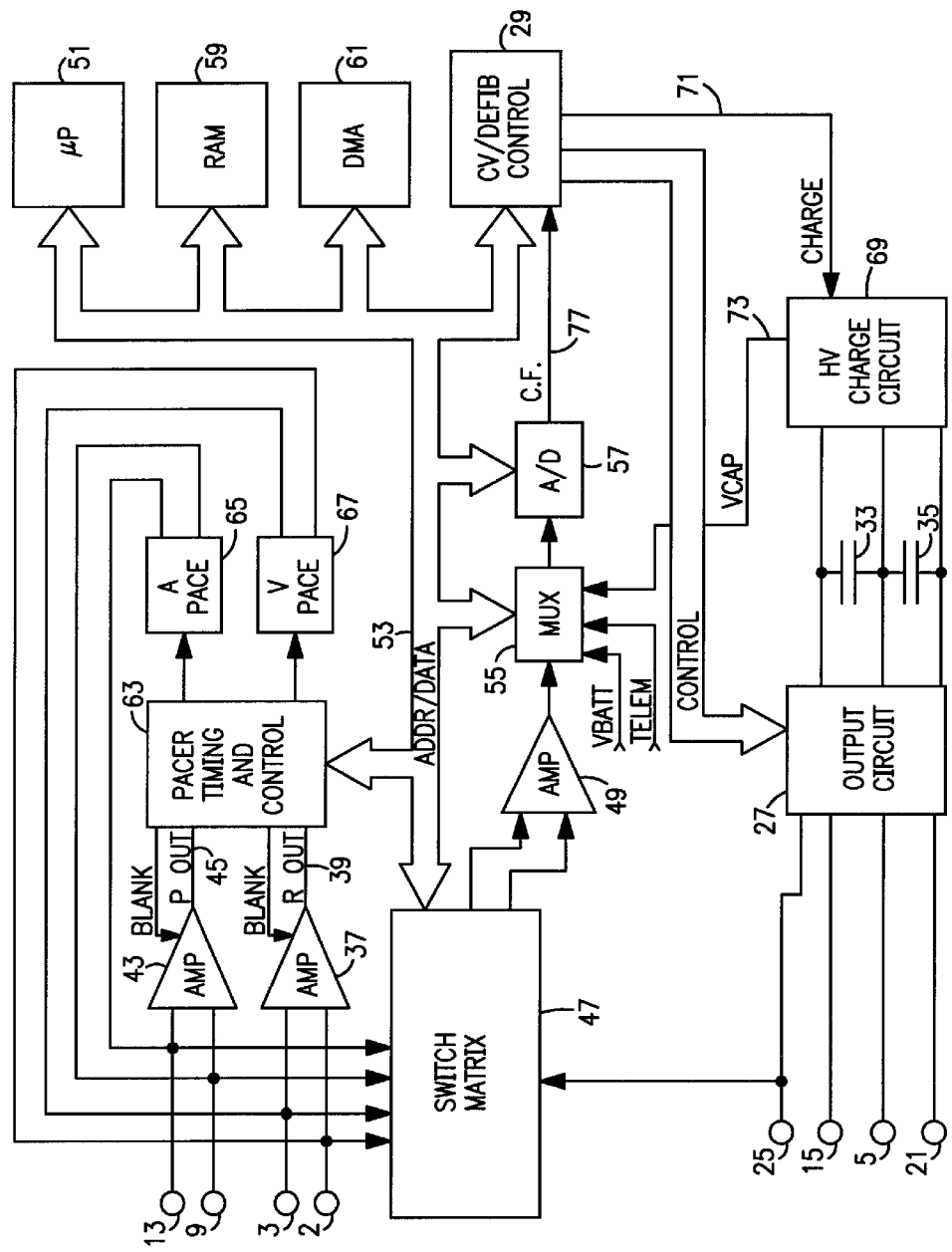
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM (memory) 59 under control of direct memory access circuit 61. Microprocessor 51 may employ digital signal analysis techniques to characterize the digitized signals stored in RAM (memory) 59 to recognize and classify the patient's heart rhythm employing any of the numerous signal-processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in RAM (memory) 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R—R intervals, P—P intervals, P-R intervals and R-P intervals, which measurements are stored in RAM (memory) 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R—R or P—P intervals of an average rate indicative of tachyarrhythmia or an unbroken series of short R—R or P—P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society Press*, pp. 167–170, also hereby incorporated by reference in its entirety. Atrial fibrillation detection methodologies are disclosed in published PCT Application Ser. No. US92/02829, Publication No. WO92/18198, by Adams et al., and in the article "Automatic Tachycardia Recognition", by Arzbaecher et al., published in *PACE*, May–June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, microprocessor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all of which are hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra, and in U.S. Pat. No. 4,727,877, both of which are hereby incorporated by reference in their entireties.

An example of circuitry that may be used to control delivery of monophasic pulses is disclosed in U.S. Pat. No. 5,163,427 to Keimel, also hereby incorporated by reference in its entirety. Output control circuitry similar to that disclosed in the '551 patent or in U.S. Pat. No. 4,800,883 to Winstrom, which is hereby incorporated by reference in its entirety, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

For purposes of the present invention, the term "capture" appearing herein may indicate the successful evocation of a stimulated response in cardiac tissue by a pacing pulse. Conversely, the term "non-capture" appearing herein may indicate the delivery of a pacing pulse to cardiac tissue that evokes an insufficient or weak stimulated response, or that evokes no stimulated response at all.

Additionally, the terms "peak tracking circuit," "capture detect circuit," "capture detection circuit" and "capture detector" appearing herein may be synonymous with one another and may indicate any one of a number of various embodiments of the circuit of the present invention that detects capture (or an evoked response or contraction) of the heart caused by the delivery of an electrical stimulus to cardiac tissue. These terms may indicate any of the various embodiments of the circuit of the present invention incorporated into an implantable medical device, into an implantable pulse generator (IPG), into a pacemaker-cardiodefibrillator (PCD) or any other cardiac stimulator.

Capture detection may be defined as the determination of whether or not a delivered pacing stimulus causes the myocardium to contract. In accordance with one aspect of the present invention, capture detection is accomplished by a capture detection circuit (CDC) (shown in FIGS. 6 and 7 as reference numeral 60). These CDCs can use the evoked signals (i.e., signals from the myocardium in response to a delivered pacing stimulus) to discriminate between captured and non-captured beats. Furthermore, additional output circuitry may be employed to enhance capture detection capabilities by reducing the effects of after potential signals.

One challenge of capture detection is to discriminate successfully between an evoked response signal and an after-potential artifact signal created by the tissue-electrode interface. In accordance with one aspect of the present invention, after-potential artifact signal rejection is accomplished by peak tracking the pacing electrode potential with respect to VDD voltage. During the capture detect window, the operation of the output circuitry and the nature of the electrode-tissue interface are such that the after-potential generally presents itself as a negatively pseudo-exponentially decaying artifact across the pacing electrode and indifferent electrode.

In one embodiment of the invention, a CDC circuit 60 may therefore be a negative peak tracking (NPT) circuit which peak tracks the current output of a differential amplifier through a large (e.g., 1.6 MΩ) resistor and subtracts the peak-tracked after-potential signal from the sense signal output by a differential amplifier circuit. In other words, a CDC circuit 60 of the present invention may detect changes in the polarity of the output of a differential amplifier circuit, where the term "polarity" refers here to the sign of the derivative (dv/dt) of the output signal provided by the differential amplifier circuit. Because the after-potential signal typically manifests itself as a pseudo-exponentially decaying artifact, any change in the polarity of the output provided by the differential amplifier circuit may be attributed to an evoked response signal. By filtering out or subtracting the evoked response signal from the output of the differential amplifier circuit, the current entering a sense-output (SO) node relates to signal deflections that are in a direction opposite to that of the tracking signal. Any artifact substantially attributable to the post-pace electrode polarization signal is thus filtered out.

Figure 6:
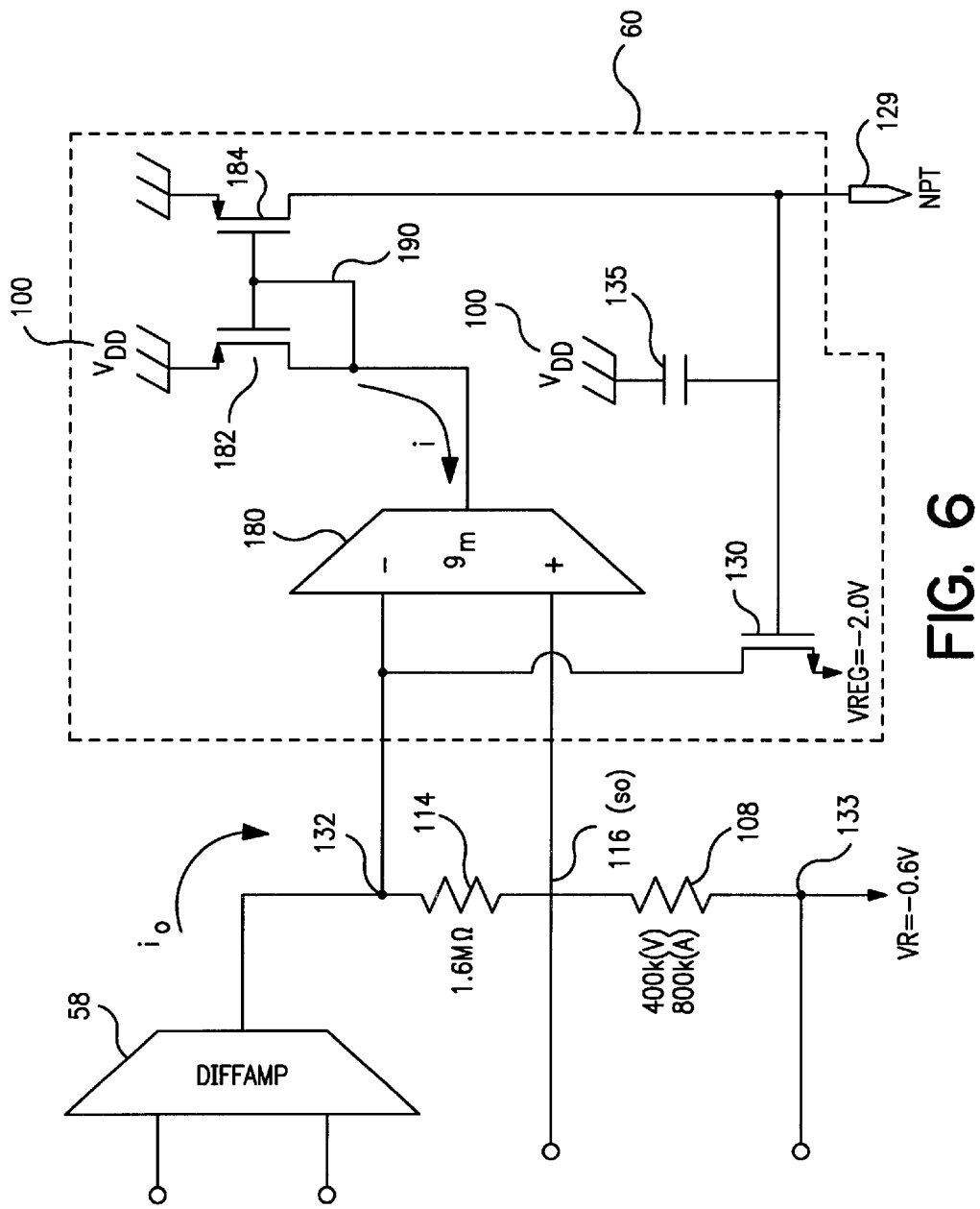
FIG. 6 is a block diagram of one embodiment of a capture detection circuit, made in accordance with the present invention.

FIG. 6 shows a more detailed functional block diagram of one embodiment of an NPT CDC 60. FIG. 6 shows that CDC 60 may include transconductance differential amplifier 180 and two transistors 182 and 184 that function as a diode between amplifier 180 and VDD. As previously noted, CDC 60 monitors the output from the differential amplifier circuit 58 through resistor 114. Like a ratchet that engages in one direction only, the voltage at node VNPT 129 can only increase towards VDD, and thus only turn on N-channel transistor 130 to a greater extent. As transistor 130 turns on more fully, more current originating at node 132 from the output of the differential amplifier circuit 58 flows through transistor 130. Thus, only current excursions less than the most recent peak-tracked current are passed to resistor 108.

That is, CDC 60 is essentially a feedback loop that attempts to zero the current flowing through resistor 114, and that may only increase the current being subtracted from node 132. Capacitor 135 facilitates this one-way or "ratcheting" effect by preventing the voltage applied to the gate of transistor 130 from falling when the sensed signal (i.e., the output of differential amplifier circuit 58) increases.

Figure 7A:
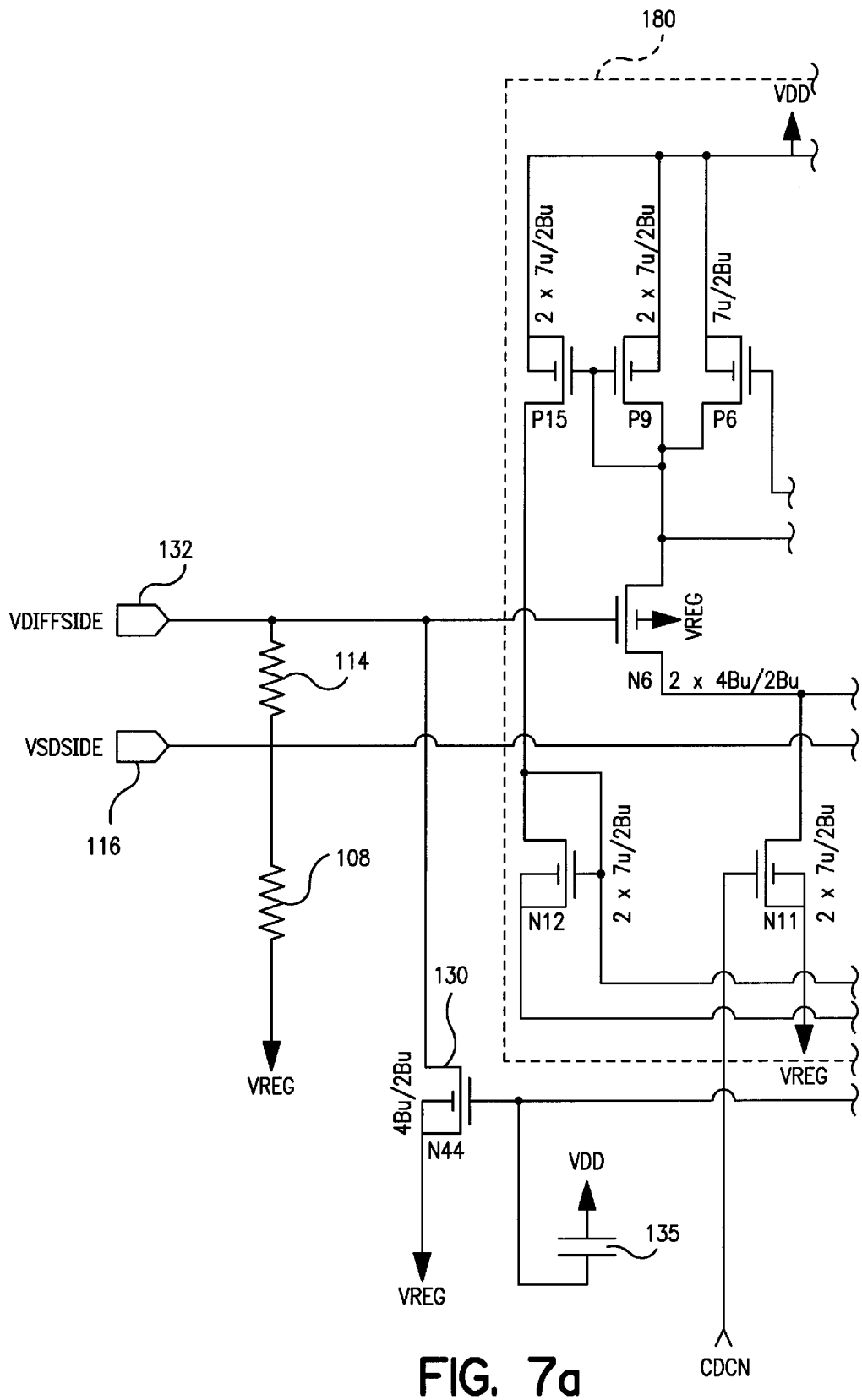
FIGS. 7a–c are more detailed block diagrams of an embodiment of the capture detection circuit of FIG. 6, made in accordance with the present invention.
Figure 7B:
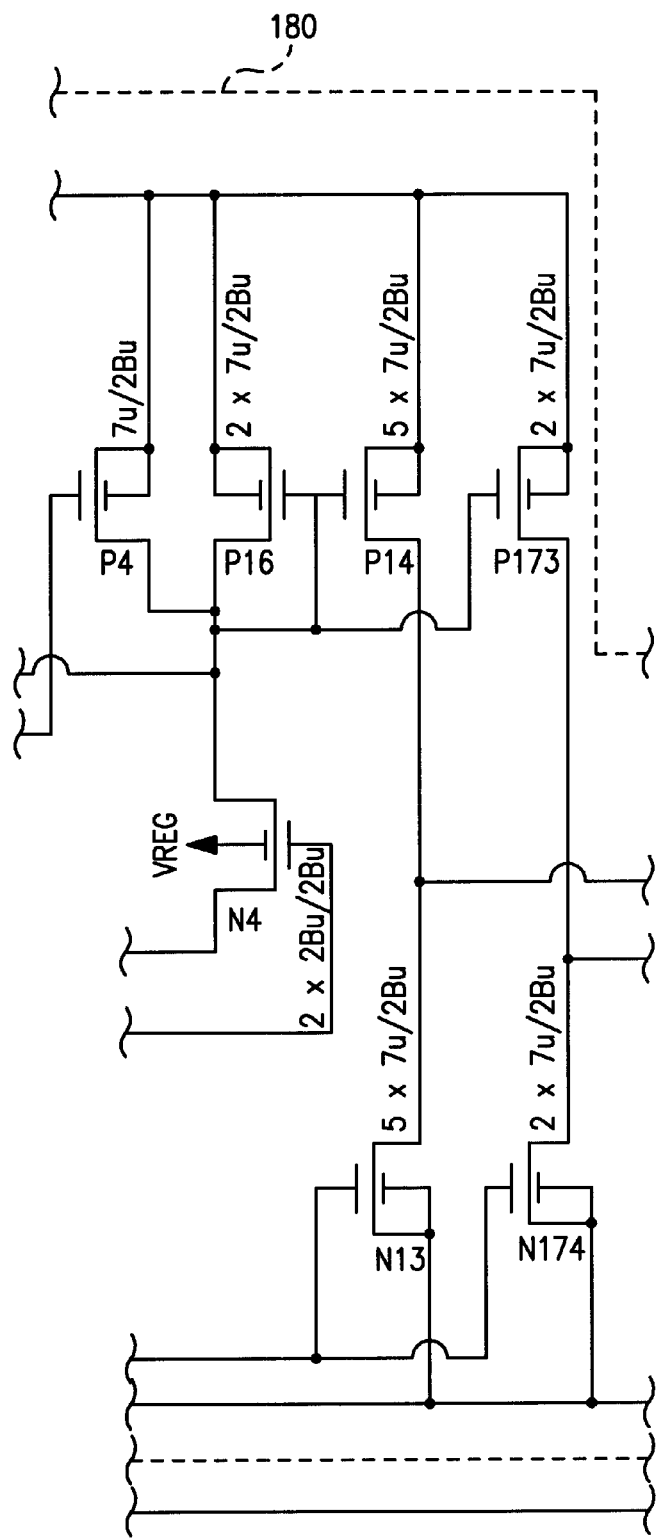
Figure 7C:
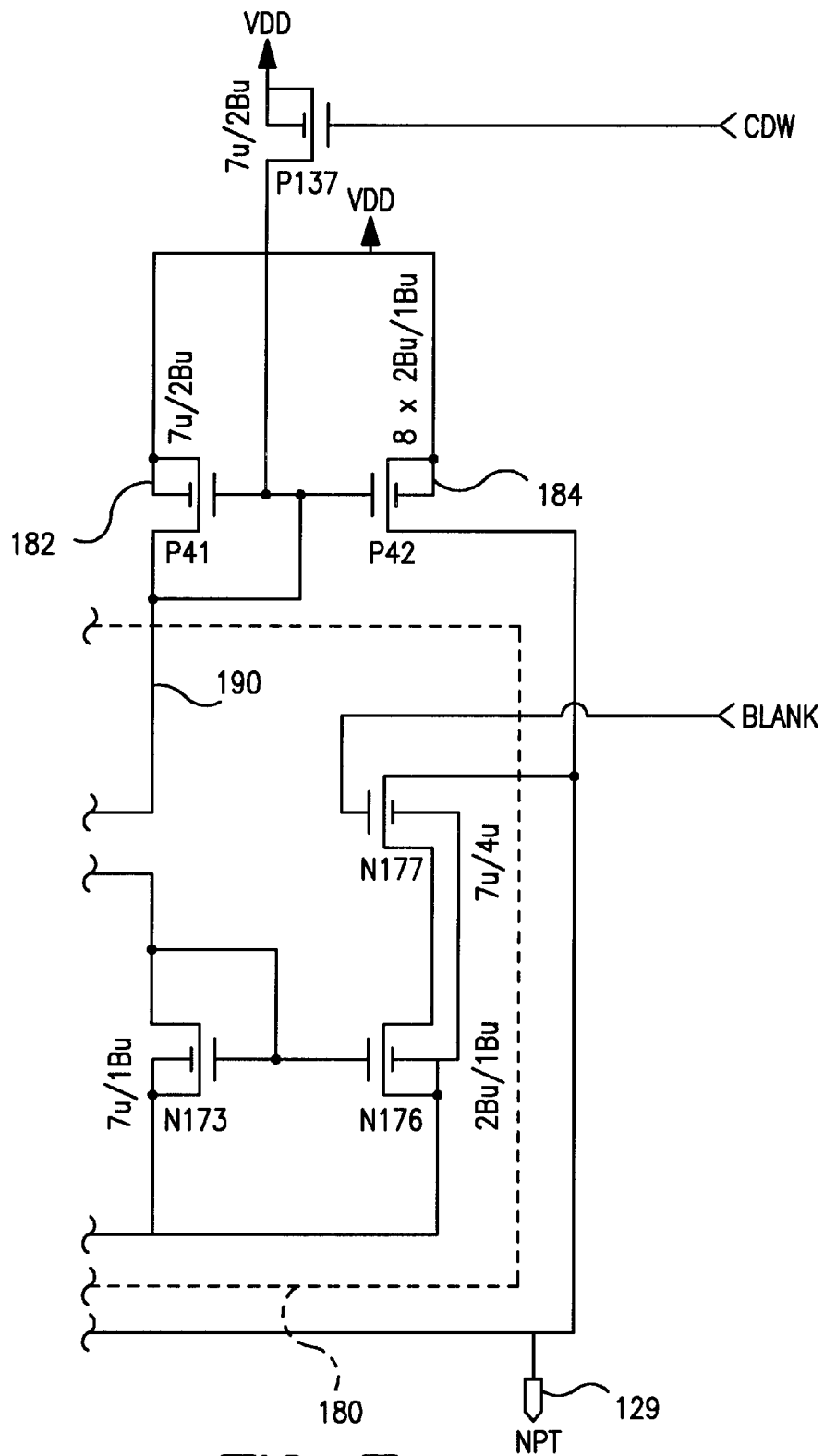

FIGS. 7a–7c show more detailed schematic circuit diagrams of another embodiment of the CDC 60 of the present invention. As in FIG. 6, differential amplifier circuit 58 is coupled to CDC 60 at node 132. Sixteen-hundred kilo-ohm resistor 114 couples nodes 132 and 116. Four hundred kilo-ohm or 800 kΩ pull-up resistor 108 (corresponding to the ventricular and atrial channels, respectively) is disposed between node 116 and a −0.6 V regulated voltage source. FIGS. 7a–7c show several additional inputs CDW, CDCN and BLANK. Inputs CDW (Capture Detect Window) and CDCN (Capture Detect Control) activate CDC 60 when capture detection is desired. Input BLANK is for blanking CDC 60, for example, during pacing.

In respect of a low polarization lead positioned in the ventricle, the embodiments of the present invention described heretofore do not significantly filter the evoked response, and thus result in an acceptable signal-to-noise ratio (SNR) being obtained in the case of evoked response signal detection. For larger pacing energies, high polarization leads, or atrial evoked response detection, a greater SNR may be desirable. This is because in these (and perhaps other) situations, the after-potential artifact may dominate the pacing electrode voltage to such an extent that no positive deflections occur in the sensed signal.

The capture detection circuitry of one embodiment of the present invention may include additional peak tracking circuitry for peak tracking the diode current in CDC 60 itself. This additional circuitry is referred to herein as "second order" peak tracking circuitry. This circuitry adds current to node 116 if the tracking current increases. In other words, when the current flowing through transistor 182 on line 190 in FIG. 6 increases, more current is provided at node 116. The increase reflects an "acceleration" or increasing magnitude of the derivative (dv/dt) of the output signal provided by the differential amplifier circuit 58. The "acceleration" occurs when the post-pace after-potential signal dominates the evoked response signal to such an extent that no reversal of polarity in the sensed signal occurs. By detecting acceleration, or an increase in the magnitude of dv/dt, in the sensed signal, it has been discovered that the evoked response may be faithfully detected.

Figure 8:
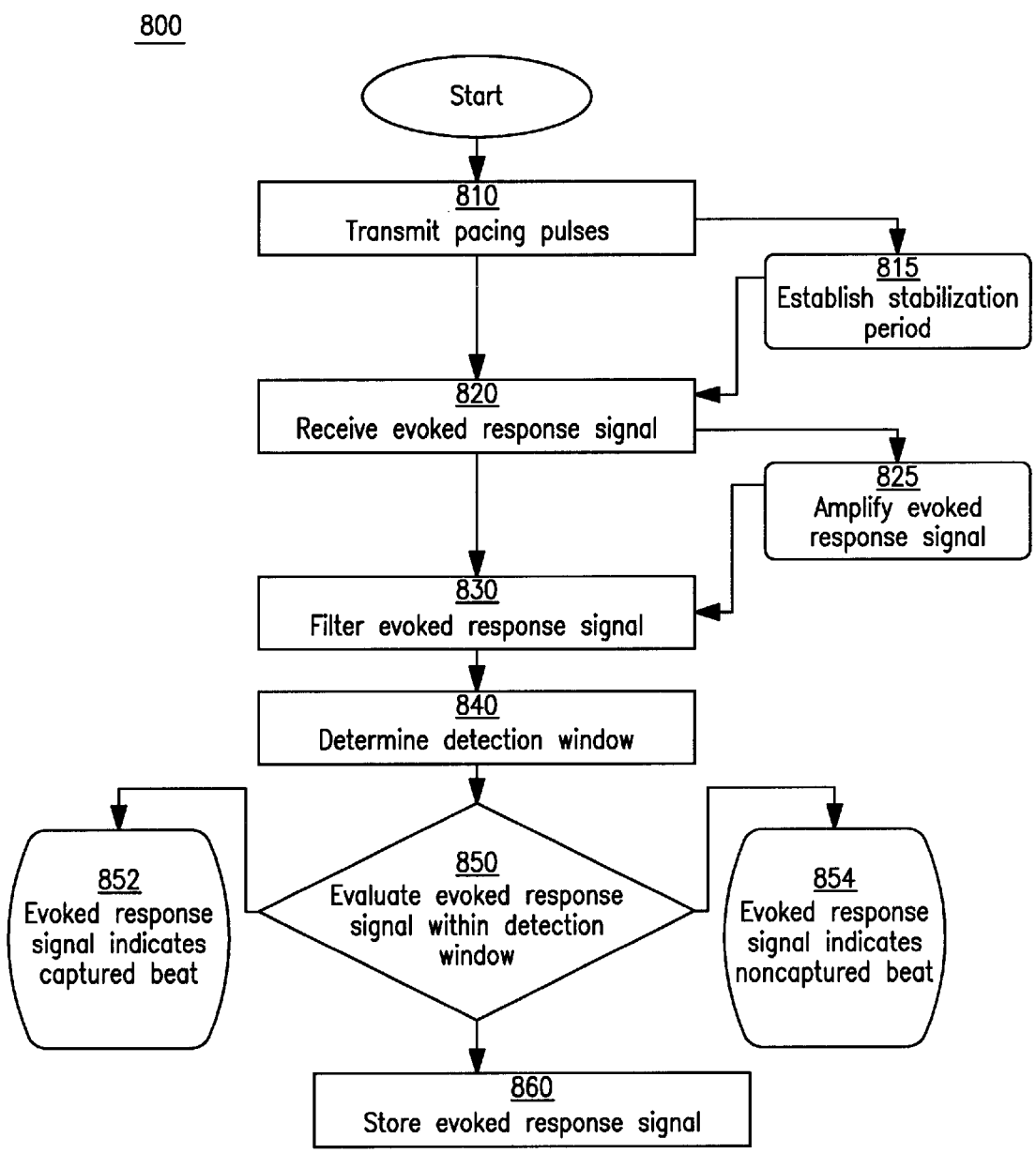
FIG. 8 is a flow diagram of one embodiment of a method for discriminating a captured beat from a non-captured beat in accordance with the present invention.

FIG. 8 illustrates a flow chart of one embodiment of a method for discriminating a captured beat from a non-captured beat in cardiac tissue at 800.

Method 800 may be particularly useful whenever an evoked response needs to be detected right after a change has occurred, for example during a threshold test. During a threshold test, as soon as the amplitude drops one step, a relatively high downward deflection of the polarization signal occurs. This deflection may be falsely interpreted as a captured beat.

At block 810, pacing pulses may be transmitted to the cardiac tissue of heart 8. Pacing of mammalian or human heart 8 may occur through the process of transmitting a plurality of stimulus pulses to mammalian or human heart 8 from electrodes 2, 3, 9, and 13. Electrodes 2, 3, 9, 13 may receive pacing signals from pacer timing/control circuitry 63 through atrial pacer output circuitry 65 and ventricular pacer output circuitry 67.

As seen at block 815, the pacing pulses transmitted may be used to establish a stabilization interval. Thus, the number of pacing pulses may be any number capable of providing for a stabilization interval, such as, for example, 20 or less. The stabilization interval may correspond to the minimum time period necessary to achieve a safe, regular heart rate for the patient. After establishing a stabilization interval, pacer timing/control circuitry 63 may maintain the stabilization interval. Adjustments to the stabilization interval may be made. Such adjustments may be input from pacer timing/control circuitry 63 from microprocessor 51, and may be directed by microprocessor 51 as a result of any number of factors, such as, for example, physician instructions or directives. The adjustments may be made depending on the electrode type and the magnitude of change. After stabilization, capture or loss of capture by evoked response sensing may be verified.

One or more of the pacing pulses at block 810 may be test pulses. In one embodiment of the invention, the distance between a test pulse and a regular pacing pulse is small enough to avoid pacing into the vulnerable phase in case of capture on the test-pulse, but still allows time to sense the evoked P- or R-wave after the test pulse. During this period no hazardous situations occur because the test pulse is always followed by a regular pulse, which is set to a safe value above threshold.

In one embodiment of the invention, a stabilization period is established only when the pacing pulses have been inhibited for a long period of time. Alternatively, a stabilization period may be established when output parameters, such as pulse width or amplitude, have been changed. Alternatively, a stabilization period may not be established for the present invention.

At block 820, an evoked response signal is received. For example, IMD 10 may receive an evoked response signal through microprocessor 51.

At block 825, the evoked response signal may be amplified to improve measurement and detection of the signal. In one embodiment of the invention, the evoked response signal is amplified using any suitable sense amplifier circuit. The sense amplifier circuit may be configured to detect the presence of intrinsic atrial and ventricular signals. Upon detecting such signals, the sense amplifier circuit may generate at least one digital output signal corresponding to the signal. The sense amplifier circuit may also be capable of detecting an evoked response signal. Upon detecting such a response, the sense amplifier circuit may generate at least one digital output signal corresponding to the evoked response signal. In one embodiment of the invention, the evoked response signal may not be amplified.

At block 830, the evoked response signal may be filtered to remove background and unnecessary noise from the evoked response signal. In one embodiment of the invention, the signal is filtered using a band-pass filter circuit. Alternatively, any suitable filter that rejects undesired low- and high-frequency components of input signals may be used. In one embodiment of the invention, the filter is used to increase the signal-to-noise ratio of coherent components of input signals. A band-pass filter circuit or other suitable filter may be implemented in either analog or digital form. For example, in a digital implementation, the band-pass filter circuit may comprise any one of several widely and commercially available digital signal processing chips.

The steps described in blocks 825 and 830 may be used to optimize polarization for examination within a detection window. Without such polarization optimization, there is no easy way to detect the evoked response signal superimposed on the polarization voltage. After polarization optimization, a simple negative level detector may be used to detect the evoked P or R waves.

Thus, at block 840, a detection window may be determined. In one embodiment of the invention, the detection window may be a post-stimulus interval. By varying only the post-stimulus interval, the evoked response signal can be adjusted in such a way that the start of the evoked response signal can be mostly negative, almost zero or positive. In one embodiment of the invention, the detection window may be a period lasting from approximately 30 to 60 ms after a stimulus, such as a pacing pulse, has been received. The detection window may be determined automatically, for example by configuring device 10 to determine a detection window. The window may also be assigned manually, for example using manual input from a user to configure device 10.

At block 850, the evoked response signal is evaluated (i.e., signal discrimination is evaluated). In one embodiment of the invention, the evoked response signal is evaluated for the period demarcated by the detection window. The evaluation may determine that the filtered evoked response signal also indicates a captured beat as seen at block 852. For example, a filtered evoked response signal showing a positive part in the detection window may indicate a captured beat. Alternatively, the evaluation may determine that the filtered evoked response signal indicates a non-captured beat, e.g., a Loss of Capture (LOC) event, as seen at block 854. For example, a filtered evoked response signal showing a negative part in the detection window may indicate a non-captured beat.

At block 860, the filtered evoked response signal may be stored. For example, microprocessor 51 may store the filtered evoked response signal in RAM (memory) 59. The filtered evoked response signal may also be saved with other information regarding the filtered evoked response signal.

Figure 9:
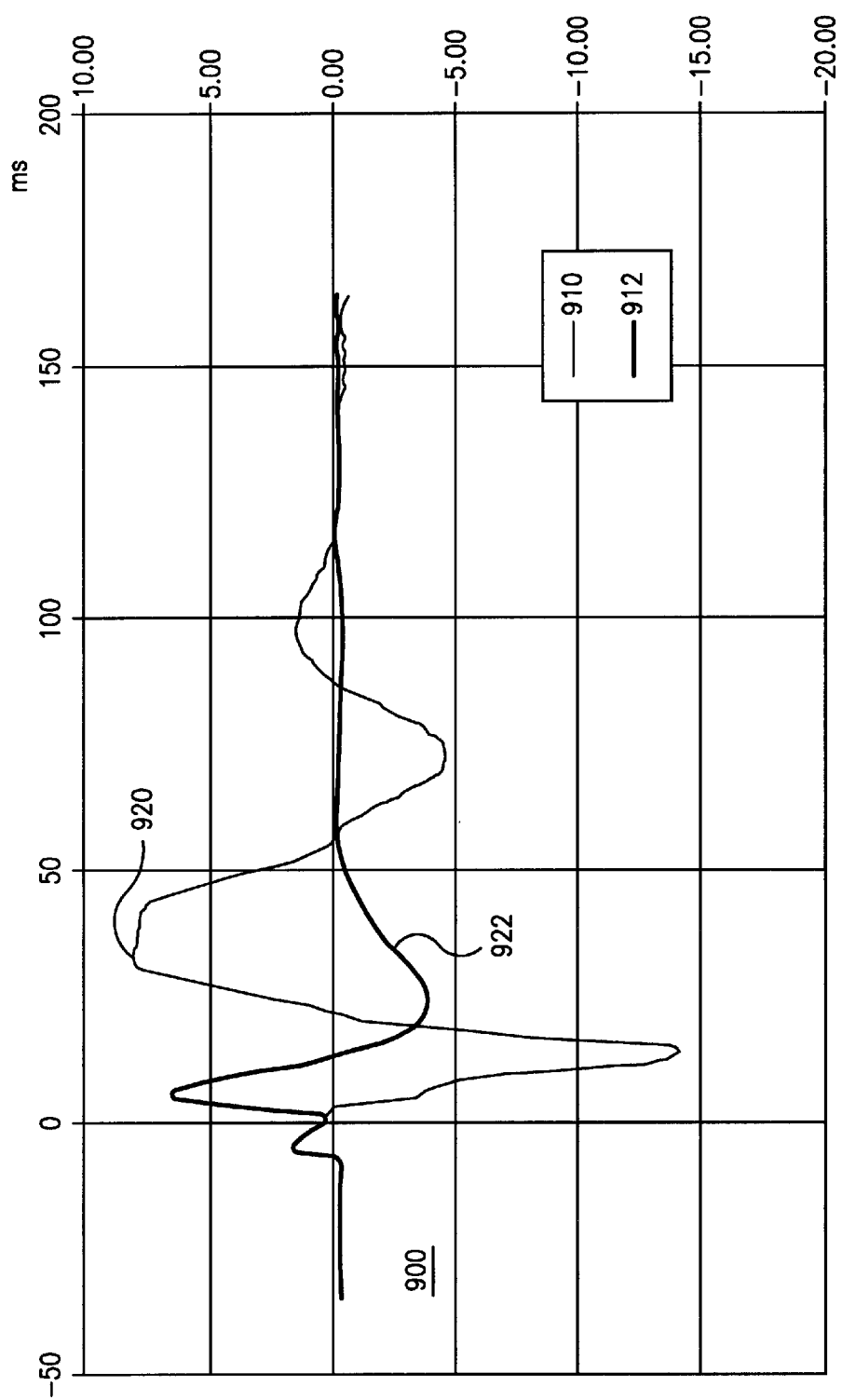
FIG. 9 is a graphic representation of a captured and a non-captured beat determined using an embodiment of the method of FIG. 8 in accordance with the present invention.

FIG. 9 shows a graphic representation of both a captured and a non-captured beat determined using an embodiment of the method of FIG. 8 in accordance with the present invention at 900. Graphic representation 900 illustrates a filtered evoked response and a filtered response of a non-captured beat in the same graph.

Line 910 may be a linear representation, or profile, of a previous evoked response as described above at block 850. In one embodiment of the invention, the previous evoked response is a captured beat. The points comprising line 910 may represent a signal from a captured beat as measured over a time interval beginning at −40 ms (before time 0) and ending at 180 ms (past time 0). This signal may be measured, for example, in mV. As seen at time 0 ms, line 910 has a value of nearly 0 mV. However, by time 35 ms, line 910 has a distinctly positive value of approximately 8 mV. This positive value is indicated at 920.

Meanwhile, line 912 may be a linear representation, or profile, of a filtered signal as described above at block 850. The points comprising line 912 may represent a signal from a non-captured beat as measured over a time interval beginning at −40 ms (before time 0) and ending at 180 ms past time 0. This signal may be measured, for example, in mV. As seen at time 0, line 912 has a value of nearly 0 mV. However, by time 35 ms, line 912 has a distinctly negative value of approximately −4 mV. This negative value is indicated at 922. When the values of lines 910 and 912 are compared, particularly at time 35 ms, the method of the present invention enables discrimination between the captured beat delineated by line 910 and the non-captured beat delineated by line 912.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method for discriminating between captured and non-captured beats in a mammalian heart. The present invention is also not limited to the discrimination of captured versus non-captured beats, per se, but may find further application as an evaluation means. The present invention further includes within its scope methods of making and using the evaluation means described hereinabove.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

I claim:

1. A method of discriminating a captured beat in cardiac tissue, comprising:

transmitting a pulse to the cardiac tissue;

receiving an evoked response signal;

filtering the evoked response signal to a filtered response signal; and analyzing the filtered response signal for at least one positive signal component.

2. The method of claim 1 further comprising:

determining a signal window; and analyzing the filtered response signal for at least one positive signal component within the signal window.

3. The method of claim 1 further comprising:

identifying the filtered response signal as the captured beat when at least one positive signal component is found.

4. The method of claim 1 further comprising:

identifying the filtered response signal as a non-captured beat when no positive signal component is found.

5. The method of claim 1 further comprising:

identifying the filtered response signal as a non-captured beat when a negative signal component is found.

6. The method of claim 1 further comprising:

determining a signal window; and analyzing the filtered response signal for at least one negative signal component within the signal window.

7. The method of claim 1 further comprising:

identifying the filtered response signal as a non-captured beat when at least one negative signal component is found.

8. The method of claim 1 further comprising:

identifying the filtered response signal as the captured beat when no negative signal component is found.

9. The method of claim 1, further comprising:

transmitting at least one pacing pulse for a predetermined stabilization period prior to transmitting the pulse.

10. The method of claim 1 further comprising:

transmitting a test pulse prior to transmitting the pulse.

11. The method of claim 1, further comprising:

storing the filtered response signal within a memory location.

12. The method of claim 11, further comprising:

accessing the filtered response signal from the memory location.

13. The method of claim 1, further comprising:

amplifying the evoked response signal.

14. An implantable medical device for distinguishing a captured beat from a non-captured beat in cardiac tissue comprising:

a processor;

a controller operably connected to the processor;

at least one sensing lead operably connected to the controller for receiving a response signal; and a filter for filtering the response signal to a filtered signal;

wherein the captured beat is distinguished from the non-captured beat by analyzing the filtered signal for at least one positive signal component.

15. The implantable medical device of claim 14 wherein the processor is capable of determining a signal window and analyzing the filtered signal within the signal window.

16. The implantable medical device of claim 14 wherein the processor identifies the filtered signal as the captured beat when at least one positive signal component is found.

17. The implantable medical device of claim 14 wherein the processor identifies the filtered signal as the non-captured beat when no positive signal component is found.

18. The implantable medical device of claim 14 wherein the processor identifies the filtered signal as the non-captured beat when a negative signal component is found.

19. The implantable medical device of claim 14 further comprising at least one pacing lead for transmitting at least one pacing pulse, wherein the pacing lead is capable of transmitting the pacing pulse for a predetermined stabilization interval.

20. The implantable medical device of claim 14 further comprising a memory location for storing the filtered signal.

21. The implantable medical device of claim 14 further comprising an amplifier for amplifying the response signal.

22. An implantable medical system for distinguishing a captured beat from a non-captured beat in cardiac tissue, comprising:

means for transmitting a pulse to the cardiac tissue;

means for receiving a response signal;

means for filtering the response signal to a filtered signal; and means for analyzing the filtered signal for at least one positive signal component.

23. The system of claim 22 further comprising:

means for determining a signal window, wherein the filtered signal is analyzed within the signal window.

24. The system of claim 22 further comprising:

means for identifying the filtered signal as the captured beat when at least one positive signal component is found.

25. The system of claim 22 further comprising:

means for identifying the filtered signal as the non-captured beat when at least one positive signal component is not found.

26. The system of claim 22 further comprising:

means for identifying the filtered signal as the non-captured beat when a negative signal component is found.

27. The system of claim 22 further comprising:

means for storing the filtered response signal within a memory location.

28. The system of claim 27 further comprising:

means for accessing the filtered response signal from the memory location.

29. The system of claim 22 further comprising:

means for amplifying the evoked response signal.

30. A computer usable medium including a program for discriminating between a captured beat and a non-captured beat in cardiac tissue, comprising:

computer readable program code that transmits a pulse to the cardiac tissue;

computer readable program code that receives an evoked signal;

computer readable program code that filters the evoked signal to a filtered signal;

computer readable program code that analyzes the filtered signal for at least one positive signal component.

31. The program of claim 30 further comprising:

computer readable program code that determines a signal window; and computer readable program code that analyzes the filtered signal within the signal window.

32. The program of claim 30 further comprising:

computer readable program code that identifies the filtered signal as the captured beat when at least one positive signal component is found.

33. The program of claim 30 further comprising:

computer readable program code that identifies the filtered signal as the non-captured beat when no positive signal component is found.

34. The program of claim 30 further comprising:

computer readable program code that analyzes the filtered signal for at least one negative signal component.

35. The program of claim 30 further comprising:

computer readable program code that identifies the filtered signal as the non-captured beat when a negative signal component is found.

36. The program of claim 30 further comprising:

computer readable program code that transmits at least one pacing pulse to the cardiac tissue for a predetermined stabilization interval.

37. The program of claim 30 further comprising:

computer readable program code that transmits at least one test pulse.

38. The system of claim 30 further comprising:

computer readable program code that amplifies the evoked signal.

39. The program of claim 30 further comprising:

computer readable program code that stores the filtered signal within a memory location.

40. The system of claim 39 further comprising:

computer readable program code that accesses the filtered response signal from the memory location.

* * * * *